United States Patent
Fleckenstein et al.

(10) Patent No.: US 9,938,548 B2
(45) Date of Patent: Apr. 10, 2018

(54) PROCESS FOR PREPARING (METH)ACRYLIC ESTERS OF FUNCTIONALIZED FURYL ALCOHOLS

(71) Applicant: BASF SE, Ludwigshafen am Rhein (DE)

(72) Inventors: Christoph Fleckenstein, Freigericht-Somborn (DE); Mathieu Blanchot, Lambsheim (DE); Benoit Blank, Edingen-Neckarhausen (DE); Martin Kaller, Mannheim (DE); Ulrik Stengel, Birkenau (DE); Andrea Misske, Speyer (DE); Friederike Fleischhaker, Ludwigshafen (DE); Ritesh Nair, Heidelberg (DE)

(73) Assignee: BASF SE, Ludwigshafen am Rhein (DE)

(*) Notice: Subject to any disclaimer, the term of this patent is extended or adjusted under 35 U.S.C. 154(b) by 0 days.

(21) Appl. No.: 14/974,267

(22) Filed: Dec. 18, 2015

(65) Prior Publication Data

US 2016/0186220 A1    Jun. 30, 2016

Related U.S. Application Data

(60) Provisional application No. 62/095,097, filed on Dec. 22, 2014.

(51) Int. Cl.
| | |
|---|---|
| C07C 47/40 | (2006.01) |
| C07C 69/54 | (2006.01) |
| C12P 17/04 | (2006.01) |
| C07D 307/46 | (2006.01) |
| C08F 220/28 | (2006.01) |
| C09D 133/14 | (2006.01) |

(52) U.S. Cl.
CPC ........... *C12P 17/04* (2013.01); *C07D 307/46* (2013.01); *C08F 220/28* (2013.01); *C09D 133/14* (2013.01); *C08F 2220/282* (2013.01)

(58) Field of Classification Search
None
See application file for complete search history.

(56) References Cited

U.S. PATENT DOCUMENTS

2009/0018300 A1* 1/2009 Bloom .................... C08G 61/12
                                                              527/102
2014/0272694 A1    9/2014 Goan et al.

FOREIGN PATENT DOCUMENTS

| DE | 33 09 564 A1 | 9/1984 |
| DE | 42 37 030 A1 | 5/1994 |
| DE | 10 2005 037 430 A1 | 2/2007 |
| EP | 0 675 141 A1 | 10/1995 |
| EP | 0 738 740 A1 | 10/1996 |
| EP | 1 375 530 B1 | 12/2005 |
| EP | 1 923 454 A1 | 5/2008 |
| EP | 1 958 944 A1 | 8/2008 |
| EP | 2 246 403 A1 | 11/2010 |
| EP | 2 781 961 A1 | 9/2014 |
| WO | WO 01/23484 A2 | 4/2001 |
| WO | WO 2006/005491 A1 | 1/2006 |
| WO | WO 2006/086322 A1 | 8/2006 |

OTHER PUBLICATIONS

Krystof et al. (ChemSusChem 2013, 6, 630-634).*
International Search Report and Written Opinion of the International Searching Authority dated Jun. 7, 2016 in PCT/EP2015/080076 (with partial English translation).

* cited by examiner

Primary Examiner — Vu A Nguyen
(74) Attorney, Agent, or Firm — Oblon, McClelland, Maier & Neustadt, L.L.P.

(57) ABSTRACT

The invention relates to a process for preparing a compound of the formula (I),

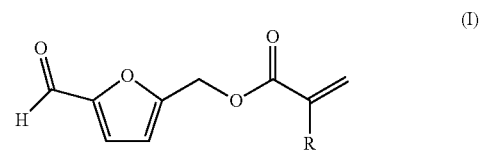

in which R is H or $C_1$-$C_6$ alkyl,
by reaction of at least one compound of the formula (II)

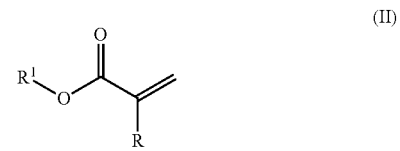

in which R has the same definition as in the formula (I) and in which $R^1$ is H, $C_1$-$C_{12}$ alkyl or $C_3$-$C_{12}$ cycloalkyl, with a compound of the formula (III)

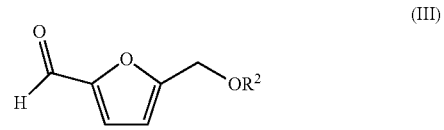

in which $R^2$ is H or $C(O)R^3$,
in which $R^3$ is H or $C_1$-$C_{12}$ alkyl,
in the presence of at least one enzyme suitable for transesterification.

11 Claims, No Drawings

PROCESS FOR PREPARING (METH)ACRYLIC ESTERS OF FUNCTIONALIZED FURYL ALCOHOLS

The invention relates to a process for preparing particular esters based on hydroxymethylfurfural (HMF), more particularly to a process for preparing HMF acrylate or HMF methacrylate. The invention further relates to the esters themselves, more particularly HMF acrylate or HMF methacrylate. Further subjects of the invention are the use thereof as monomers or comonomers in the preparation of dispersions, and the use thereof for the preparation of crosslinkable copolymers.

HMF, which can be obtained from sugars, is a highly promising synthetic building block from renewable raw materials.

Described in US 2009/0018300 and in Polymer Reprints 2008, 914-915 is the preparation of HMF acrylate by reaction of HMF with acryloyl chloride, using stoichiometric quantities of triethylamine. This synthesis, however, has a number of drawbacks, particularly in relation to its implementation on an industrial scale.

For example, in the course of the reaction, triethylammonium hydrochloride is produced, and this not only necessitates the possibly problematic handling of a solid, but may also lead to yield losses as it is removed. Also a drawback are the use of a highly reactive acyl chloride and the associated release of chloride, since this imposes restrictions on the selection of materials for production plant and since appropriately resistant materials are expensive. Likewise a drawback is that the reaction has to be carried out in the absence of moisture, since acyl chlorides are hydrolytically unstable. The reaction with acyl chlorides, moreover, leads in general to products which have a relatively dark coloration and a relatively high chloride content.

The object of the invention lies in the provision of a process with which the drawbacks identified above are overcome, and which can be carried out on an industrial scale as well.

The object is achieved by means of a process for preparing a compound of the formula (I),

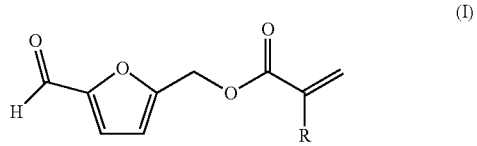

(I)

in which R is H or $C_1$-$C_6$ alkyl,
by reaction of at least one compound of the formula (II)

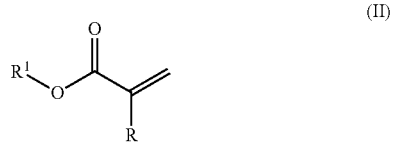

(II)

in which R has the same definition as in the formula (I) and
in which $R^1$ is H, $C_1$-$C_{12}$ alkyl or $C_3$-$C_{12}$ cycloalkyl, with a compound of the formula (III)

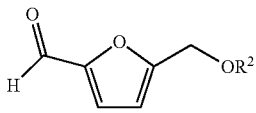

(III)

in which $R^2$ is H or $C(O)R^3$,
in which $R^3$ is H or $C_1$-$C_{12}$ alkyl,
in the presence of at least one enzyme suitable for transesterification.

It has been found that the enzymatic reaction is highly selective and that products with a high purity are obtained. The enzymatic reaction can also be carried out on an industrial scale.

The process of the invention is carried out in the presence of at least one enzyme suitable for transesterification, meaning that it is necessary neither to handle nor to remove any saltlike solid arising in stoichiometric quantities, such as triethylammonium hydrochloride. Furthermore, the process of the invention starts not from highly reactive acyl chlorides, but instead from carboxylic acids or esters, and so poses no particular challenges in terms of chloride corrosion to the materials for production plant, but can instead be carried out without difficulties in customary apparatus. Another benefit of the process of the invention is that it does not have to be carried out under strict exclusion of moisture. Also of benefit, not least in view of a certain instability on the part of HMF toward temperature and acid, is that the process of the invention can be carried out under mild reaction conditions, such as at relatively low temperatures. The enzymatic reaction leads to much paler products with a much lower chloride content than the reaction with acyl chlorides. In comparison to conventional transesterifications or direct esterifications, which often require relatively high temperatures, the process of the invention also affords much paler products. The enzymatic reaction is highly selective, and products with a high purity are obtained.

In accordance with the invention, R in the formula (I) is H or $C_1$-$C_6$ alkyl.

Examples of $C_1$-$C_6$ alkyl are methyl, ethyl, n-propyl, isopropyl, n-butyl, isobutyl, sec-butyl, tert-butyl, n-pentyl, isopentyl, sec-pentyl, tert-pentyl, neopentyl, hexyl.

In one preferred embodiment of the invention, R in the formula (I) is H or $C_1$-$C_4$ alkyl.

Examples of $C_1$-$C_4$ alkyl are methyl, ethyl, n-propyl, isopropyl, n-butyl, isobutyl, sec-butyl, tert-butyl.

In one particularly preferred embodiment of the invention, R in the formula (I) is H or $CH_3$.

In an especially preferred embodiment of the invention, R in the formula (I) is H.

In a further especially preferred embodiment of the invention, R in the formula (I) is $CH_3$.

In another embodiment of the invention, R in the formula (I) is $C_1$-$C_6$ alkyl.

In another embodiment of the invention, R in the formula (I) is $C_1$-$C_4$ alkyl.

In accordance with the invention, R in the formula (II) has the same definition as R in the formula (I).

Preferred for R in the formula (II) is the definition preferred for R in the formula (I).

Particularly preferred for R in the formula (II) is the definition particularly preferred for R in the formula (I).

Especially preferred for R in the formula (II) is the definition especially preferred for R in the formula (I).

In accordance with the invention, R in the formula (II) is H, $C_1$-$C_{12}$ alkyl or $C_3$-$C_{12}$ cycloalkyl.

Examples of $C_1$-$C_{12}$ alkyl are methyl, ethyl, n-propyl, isopropyl, n-butyl, isobutyl, sec-butyl, tert-butyl, n-pentyl, isopentyl, sec-pentyl, tert-pentyl, neopentyl, hexyl, heptyl, octyl, especially 2-ethylhexyl, nonyl, especially isononyl, decyl, especially 2-propylheptyl, undecyl, dodecyl.

Examples of $C_3$-$C_{12}$ cycloalkyl are cyclopropyl, cyclobutyl, cyclopentyl, cyclohexyl, cycloheptyl, cyclooctyl, cyclononyl, cyclodecyl, cycloundecyl, cyclododecyl.

In one preferred embodiment of the invention, $R^1$ in the formula (II) is $C_1$-$C_{12}$ alkyl.

In one particular embodiment of the invention, $R^1$ in the formula (II) is methyl, ethyl, n-propyl, isopropyl, n-butyl, isobutyl, sec-butyl, tert-butyl, or 2-ethylhexyl.

In another preferred embodiment of the invention, $R^1$ in the formula (II) is H or $C_1$-$C_4$ alkyl.

Examples of $C_1$-$C_4$ alkyl are methyl, ethyl, n-propyl, isopropyl, n-butyl, isobutyl, sec-butyl, tert-butyl.

In one particularly preferred embodiment of the invention, $R^1$ in the formula (II) is $C_1$-$C_4$ alkyl.

In one especially preferred embodiment of the invention, $R^1$ in the formula (II) is $CH_3$ or $CH_2CH_3$, especially $CH_3$.

In another embodiment of the invention, $R^1$ in the formula (II) is H.

In another preferred embodiment of the invention, $R^1$ in the formula (II) is $C_1$-$C_{12}$ alkyl or $C_5$-$C_7$ cycloalkyl.

In another particular embodiment of the invention, $R^1$ in the formula (II) is methyl, ethyl, n-propyl, isopropyl, n-butyl, isobutyl, sec-butyl, tert-butyl, 2-ethylhexyl, or cyclohexyl.

In another preferred embodiment of the invention, $R^1$ in the formula (II) is H, $C_1$-$C_4$ alkyl or cyclohexyl.

In another particularly preferred embodiment of the invention, $R^1$ in the formula (II) is $C_1$-$C_4$ alkyl or cyclohexyl.

In another embodiment of the invention, $R^1$ in the formula (II) is $C_8$-$C_{10}$ alkyl, preferably 2-ethylhexyl, isononyl, or 2-propylheptyl, very preferably 2-ethylhexyl.

In another embodiment of the invention, $R^1$ in the formula (II) is $C_5$-$C_7$ cycloalkyl, preferably cyclopentyl or cyclohexyl, more preferably cyclohexyl.

Examples of compounds of the formula (II) are methyl acrylate, ethyl acrylate, n-propyl acrylate, isopropyl acrylate, n-butyl acrylate, isobutyl acrylate, sec-butyl acrylate, tert-butyl acrylate, n-pentyl acrylate, isopentyl acrylate, sec-pentyl acrylate, tert-pentyl acrylate, neopentyl acrylate, hexyl acrylate, heptyl acrylate, octyl acrylate, especially 2-ethylhexyl acrylate, nonyl acrylate, especially isononyl acrylate, decyl acrylate, especially 2-propylheptyl acrylate, undecyl acrylate, dodecyl acrylate.

Further examples of compounds of the formula (II) are methyl methacrylate, ethyl methacrylate, n-propyl methacrylate, isopropyl methacrylate, n-butyl methacrylate, isobutyl methacrylate, sec-butyl methacrylate, tert-butyl methacrylate, n-pentyl methacrylate, isopentyl methacrylate, sec-pentyl methacrylate, tert-pentyl methacrylate, neopentyl methacrylate, hexyl methacrylate, heptyl methacrylate, octyl methacrylate, especially 2-ethylhexyl methacrylate, nonyl methacrylate, especially isononyl methacrylate, decyl methacrylate, especially 2-propylheptyl methacrylate, undecyl methacrylate, dodecyl methacrylate.

Further examples of compounds of the formula (II) are acrylic acid, methacrylic acid.

In one preferred embodiment of the invention, methyl acrylate, ethyl acrylate, n-propyl acrylate, isopropyl acrylate, n-butyl acrylate, isobutyl acrylate, sec-butyl acrylate, tert-butyl acrylate, 2-ethylhexyl acrylate, methyl methacrylate, ethyl methacrylate, n-propyl methacrylate, isopropyl methacrylate, n-butyl methacrylate, isobutyl methacrylate, sec-butyl methacrylate, tert-butyl methacrylate, or 2-ethylhexyl methacrylate is used as compound of the formula (II).

In one particularly preferred embodiment of the invention, methyl acrylate, ethyl acrylate, methyl methacrylate or ethyl methacrylate is used as compound of the formula (II).

In one especially preferred embodiment of the invention, methyl acrylate is used as compound of the formula (II).

In another especially preferred embodiment of the invention, methyl methacrylate is used as compound of the formula (II).

In another embodiment of the invention, acrylic acid is used as compound of the formula (II).

In another embodiment of the invention, methacrylic acid is used as compound of the formula (II).

In accordance with the invention, at least one compound of the formula (II) is used. Preference is given to using one to three compounds of the formula (II). Particular preference is given to using one or two compounds of the formula (II). Especial preference is given to using one (1) compound of the formula (II).

The compounds of the formula (II) are available commercially or can be prepared by methods known to the skilled person.

Compounds of the formula (II) in which $R^1$ is not H may be prepared, for example, from compounds of the formula (II) in which $R^1$ is H by esterification, using for example an alcohol in the presence of an acid as catalyst.

For example, compounds of the formula (II) in which $R^1$ is methyl, ethyl or n-butyl, can be prepared from compounds of the formula (II) in which $R^1$ is H by esterification using methanol, ethanol, or n-butanol as alcohol, in the presence of an acid as catalyst.

Compounds of the formula (II) in which $R^1$ is tert-butyl can be prepared, for example, from compounds of the formula (II) in which $R^1$ is H by reaction with isobutene in the presence of an acid as catalyst.

Compounds of the formula (II) in which $R^1$ is not H can be prepared, for example, from compounds of the formula (II) in which $R^1$ is likewise not H by transesterification, using an alcohol in the presence of an acid or a base as catalyst, for example.

Compounds of the formula (II) in which $R^1$ is H may be prepared, for example, from compounds of the formula (II) in which $R^1$ is not H by hydrolysis, in the presence of an acid or a base as catalyst, for example.

In accordance with the invention, $R^2$ in the formula (III) is H or $C(O)R^3$.

In one preferred embodiment of the invention, $R^2$ in the formula (III) is H. Compounds of the formula (III) in which $R^2$ is H are referred to as compounds of the formula (IIIa):

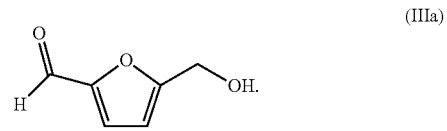

In another embodiment of the invention, $R^2$ in the formula (III) is $C(O)R^3$. Compounds of the formula (III) in which $R^2$ is $C(O)R^3$ are referred to as compounds of the formula (IIIb):

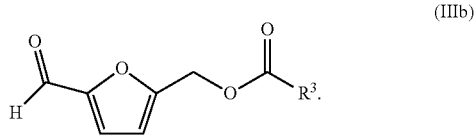

(IIIb)

In accordance with the invention, $R^3$ is H or $C_1$-$C_{12}$ alkyl.

Examples of $C_1$-$C_{12}$ alkyl are methyl, ethyl, n-propyl, isopropyl, n-butyl, isobutyl, sec-butyl, tert-butyl, n-pentyl, isopentyl, sec-pentyl, tert-pentyl, neopentyl, hexyl, heptyl, octyl, more particularly 2-ethylhexyl, nonyl, more particularly isononyl, decyl, more particularly 2-propylheptyl, undecyl, dodecyl.

In one preferred embodiment of the invention, $R^3$ is H or $C_1$-$C_8$ alkyl.

Examples of $C_1$-$C_8$ alkyl are methyl, ethyl, n-propyl, isopropyl, n-butyl, isobutyl, sec-butyl, tert-butyl, or 2-ethylhexyl.

In one particularly preferred embodiment of the invention, $R^3$ is H or $C_1$-$C_4$ alkyl.

Examples of $C_1$-$C_4$ alkyl are methyl, ethyl, n-propyl, isopropyl, n-butyl, isobutyl, sec-butyl, tert-butyl.

In one especially preferred embodiment of the invention, $R^3$ is H or $CH_3$, more particularly $CH_3$.

In another particular embodiment of the invention, $R^3$ is H.

The compounds of the formula (III) are available commercially (e.g., Aldrich) or may be prepared by methods known in the literature (B. Kim et al., Ind. Eng. Chem. Res. 2014, 53, 4633-4641; R.-J. van Putten et al., Chem. Rev. 2013, 113, 1499-1597; EP 1958944; DE 3309564).

Suitable methods for preparing the compounds of the formula (IIIb), more particularly suitable formylation or acylation methods for the introduction of the group $C(O)R^3$, are known to the skilled person.

The at least one compound of the formula (II) and the compound of the formula (III) are used in general in a molar ratio of 1:10 to 25:1, preferably of 1:1 to 20:1, more preferably of 5:1 to 15:1, very preferably of 8:1 to 12:1.

In one embodiment of the invention, $R^1$ in the formula (II) is H if $R^2$ in the formula (III) is $C(O)R^3$. In another embodiment of the invention, $R^2$ in the formula (III) is $C(O)R^3$ if $R^1$ in the formula (II) is H. In a further embodiment of the invention, $R^1$ in the formula (II) is H and $R^2$ in the formula (III) is $C(O)R^3$.

In one embodiment of the invention, $R^1$ in the formula (II) is not H if $R^2$ in the formula (III) is H. In another embodiment of the invention, $R^2$ in the formula (III) is H if $R^1$ in the formula (II) is not H. In a further embodiment of the invention, $R^1$ in the formula (II) is not H and $R^2$ in the formula (III) is H.

Used in accordance with the invention is at least one enzyme suitable for transesterification. Preference is given to using one to three enzymes. Particular preference is given to using one or two enzymes. Very particular preference is given to using one (1) enzyme.

Enzymes suitable for transesterification are known to the skilled person.

With preference a hydrolase (EC 3.-.-.-) is used as enzyme.

Examples of suitable hydrolases (EC 3.-.-.-) are esterases (EC 3.1.-.-), glycolases (EC 3.2.-.-), or proteases (EC 3.4.-.-), preferably esterases (EC 3.1.-.-) or proteases (EC 3.4.-.-).

Particular preference is given to using an esterase (EC 3.1.-.-) as enzyme.

Examples of suitable esterases (EC 3.1.-.-) are lipases (EC 3.1.1.-).

Especial preference is given to using a lipase (EC 3.1.1.-) as enzyme.

Examples of suitable lipases (EC 3.1.1.-) are triacylglycerol lipases (EC 3.1.1.3).

More particularly preferred is the use of a triacylglycerol lipase (EC 3.1.1.3) as enzyme.

Particularly preferred are Novozym® 435 (lipase from *Candida antarctica* B) or lipase from *Alcaligenes* sp., *Aspergillus* sp., *Mucor* sp., *Penicilium* sp., *Geotricum* sp., *Rhizopus* sp., *Burkholderia* sp., *Candida* sp., *Pseudomonas* sp., *Thermomyces* sp., or porcine pancreas, more particularly lipase from *Candida antarctica* B or lipase from *Burkholderia* sp., particular preference being given to lipase from *Candida antarctica* B.

The enzymes are available commercially (e.g., Novozym® 435) or may be obtained by methods known to the skilled person.

The at least one enzyme may be used in free form or in immobilized form. In one embodiment of the invention the at least one enzyme is used in free form. In another embodiment of the invention the at least one enzyme is used in immobilized form.

The at least one enzyme may be chemically or physically immobilized. Suitable supports and suitable methods for immobilization are known to the skilled person.

One example of suitable support is an acrylic resin. Another example of a suitable support is Lewatit®. A further example of a suitable support is Lewatit® VP OC 1600. Lewatit® VP OC 1600 is a macroporous, divinylbenzene-crosslinked polymer in spherical bead form, based on methacrylate. Another example of a suitable support, accordingly, is a macroporous, divinylbenzene-crosslinked polymer in spherical bead form, based on methacrylate.

In one preferred embodiment of the invention, a lipase from *Candida antarctica* B is used as enzyme.

In one particularly preferred embodiment of the invention, a lipase from *Candida antarctica* B in immobilized form is used as enzyme.

In one particular embodiment of the invention, a lipase from *Candida antarctica* B in immobilized form is used as enzyme, the support used being an acrylic resin. In another particular embodiment of the invention, a lipase from *Candida antarctica* B in immobilized form is used as enzyme, the support used being Lewatit®, more particularly Lewatit® VP OC 1600. In a further particular embodiment of the invention, a lipase from *Candida antarctica* B in immobilized form is used as enzyme, the support used being a macroporous, divinylbenzene-crosslinked polymer in spherical bead form, based on methacrylate.

An especially preferred embodiment of the invention uses Novozym® 435 as enzyme.

The at least one enzyme is used in general in an amount in the range from 0.1 to 15 wt %, preferably 1 to 10 wt %, more preferably 5 to 9 wt %, very preferably 6 to 8 wt %, based on the amount of compound of the formula (III) employed.

In one preferred embodiment of the invention, the at least one enzyme is used in immobilized form and in an amount in the range from 0.1 to 15 wt %, preferably 1 to 10 wt %, more preferably 5 to 9 wt %, very preferably 6 to 8 wt %, based on the amount of compound of the formula (III) employed.

In one particularly preferred embodiment of the invention, Novozym® 435 is used as enzyme and in an amount in the range from 0.1 to 15 wt %, preferably 1 to 10 wt %, more preferably 5 to 9 wt %, very preferably 6 to 8 wt %, based on the amount of compound of the formula (III) employed.

According to the invention, SEQ ID NO: 1 refers to the following amino acid sequence:

MKLLSLTGVAGVLATCVAATPLVKRLPSGSDPAFSQPKSVLDAGLTCQG

ASPSSVSKPILLVPGTGTTGPQSFDSNWIPLSTQLGYTPCWISPPPFML

NDTQVNTEYMVNAITALYAGSGNNKLPVLTWSQGGLVAQWGLTFFPSIR

SKVDRLMAFAPDYKGTVLAGPLDALAVSAPSVWQQTTGSALTTALRNAG

GLTQIVPTTNLYSATDEIVQPQVSNSPLDSSYLFNGKNVQAQAVCGPLF

VIDHAGSLTSQFSYVVGRSALRSTTGQARSADYGITDCNPLPANDLTPE

QKVAAAALLAPAAAAIVAGPKQNCEPDLMPYARPFAVGKRTCSGIVTP

The N-terminal 25 amino acids of SEQ ID NO: 1 may be considered a pre-propeptide, which may contain a sequence of a signal peptide and a sequence of a propeptide. Therefore, the sequence may optionally also start at the amino acid in position 26.

Preferably, the enzyme used in the present invention comprises an amino acid sequence of at least 80% homology to SEQ ID NO: 1, more preferably of at least 85% homology to SEQ ID NO: 1, even more preferably of at least 90% homology to SEQ ID NO: 1, even more preferably of at least 95% homology to SEQ ID NO: 1, even more preferably of at least 98% homology to SEQ ID NO: 1, even more preferably of at least 99% homology to SEQ ID NO: 1, and in particular an amino acid sequence of SEQ ID NO: 1. Alternatively, the enzyme used in the present invention is preferably a functional derivative thereof.

Particularly preferably, the enzyme used in the present invention consists of an amino acid sequence of at least 80% homology to SEQ ID NO: 1, more preferably of at least 85% homology to SEQ ID NO: 1, even more preferably of at least 90% homology to SEQ ID NO: 1, even more preferably of at least 95% homology to SEQ ID NO: 1, even more preferably of at least 98% homology to SEQ ID NO: 1, even more preferably of at least 99% homology to SEQ ID NO: 1, and in particular of an amino acid sequence of SEQ ID NO: 1. Alternatively, the enzyme used in the present invention is particularly preferably a functional derivative thereof.

Preferably, the enzyme used in the present invention has at least 10%, more preferably at least 20%, even more preferably at least 30%, even more preferably at least 40%, even more preferably at least 50%, even more preferably at least 60%, even more preferably at least 70%, even more preferably at least 80%, even more preferably at least 90%, or even 100% or more of the transesterification activity of an enzyme comprising, preferably consisting of, an amino acid sequence of SEQ ID NO: 1.

According to the invention, SEQ ID NO: 2 refers to the following amino acid sequence:

LPSGSDPAFSQPKSVLDAGLTCQGASPSSVSKPILLVPGTGTTGPQSFD

SNWIPLSTQLGYTPCWISPPPFMLNDTQVNTEYMVNAITALYAGSGNNK

LPVLTWSQGGLVAQWGLTFFPSIRSKVDRLMAFAPDYKGTVLAGPLDAL

AVSAPSVWQQTTGSALTTALRNAGGLTQIVPTTNLYSATDEIVQPQVSN

SPLDSSYLFNGKNVQAQAVCGPLFVIDHAGSLTSQFSYVVGRSALRSTT

GQARSADYGITDCNPLPANDLTPEQKVAAAALLAPAAAAIVAGPKQNCE

PDLMPYARPFAVGKRTCSGIVTP

Also preferably, the enzyme used in the present invention comprises an amino acid sequence of at least 80% homology to SEQ ID NO: 2, more preferably of at least 85% homology to SEQ ID NO: 2, even more preferably of at least 90% homology to SEQ ID NO: 2, even more preferably of at least 95% homology to SEQ ID NO: 2, even more preferably of at least 98% homology to SEQ ID NO: 2, even more preferably of at least 99% homology to SEQ ID NO: 2, and in particular an amino acid sequence of SEQ ID NO: 2. Alternatively, the enzyme used in the present invention is preferably a functional derivative thereof.

Also particularly preferably, the enzyme used in the present invention consists of an amino acid sequence of at least 80% homology to SEQ ID NO: 2, more preferably of at least 85% homology to SEQ ID NO: 2, even more preferably of at least 90% homology to SEQ ID NO: 2, even more preferably of at least 95% homology to SEQ ID NO: 2, even more preferably of at least 98% homology to SEQ ID NO: 2, even more preferably of at least 99% homology to SEQ ID NO: 2, and in particular of an amino acid sequence of SEQ ID NO: 2. Alternatively, the enzyme used in the present invention is particularly preferably a functional derivative thereof.

Also preferably, the enzyme used in the present invention has at least 10%, more preferably at least 20%, even more preferably at least 30%, even more preferably at least 40%, even more preferably at least 50%, even more preferably at least 60%, even more preferably at least 70%, even more preferably at least 80%, even more preferably at least 90%, or even 100% or more of the transesterification activity of an enzyme comprising, preferably consisting of, an amino acid sequence of SEQ ID NO: 2.

In a particular embodiment the enzyme used in the present invention consists of the amino acid sequence described in Structure 1994, Vol 2, No 4, pages 293-308 (Jonas Uppenberg, Mogens Trier Hansen, Shamkant Patkar, T Alwyn Jones: The sequence, crystal structure determination and refinement of two crystal forms of lipase B from *Candida antarctica*), which is hereby incorporated by reference. The amino acid sequence is disclosed on page 294, FIG. 1 and its accompanying text, of this article. As described in the accompanying text to FIG. 1, the N-terminal 25 amino acids, i.e. the amino acids-25 to -1, are referred to as a pre-propeptide. In one embodiment the enzyme is the full-length polypeptide disclosed on page 294, FIG. 1 and its accompanying text, which also includes the amino acids-25 to -1. In another embodiment the enzyme consists of the amino acid sequence disclosed on page 294, FIG. 1 and its accompanying text, which does not contain the amino acids-25 to -1. It is known to a person skilled in the art that the enzyme can also be used without the C-terminal OPA depicted in FIG. 1 on page 294.

According to the invention, the term "homology" means sequence homology and/or three-dimensional (3D) structural homology. Preferably, the term "homology" means sequence homology.

According to the invention, the term "functional derivative thereof" refers to an enzyme having at least 10%, more preferably at least 20%, even more preferably at least 30%, even more preferably at least 40%, even more preferably at least 50%, even more preferably at least 60%, even more preferably at least 70%, even more preferably at least 80%, even more preferably at least 90%, or even 100% or more of the transesterification activity of an enzyme comprising, preferably consisting of, an amino acid sequence of SEQ ID NO: 1 or SEQ ID NO: 2, respectively.

It is known to a person skilled in the art that the enzyme used in the present invention may optionally include one or more posttranslational modification(s).

It is known to a person skilled in the art that the enzyme used in the present invention may optionally be conjugated or bound to one or more other molecule(s). Examples of such other molecules include fluorescent molecules. An example of a fluorescent derivatization reagent is ortho-phthaldialdehyde (OPA).

It is known to a person skilled in the art that the enzyme used in the present invention may optionally be labeled with different isotopes, such as $^2H$, $^3H$, $^{13}C$, $^{14}C$, $^{32}P$ and/or $^{35}S$.

The process of the invention is carried out optionally in the presence of one or more further additives.

Examples of further additives are stabilizers, molecular sieves, or zeolites. Suitable stabilizers, molecular sieves, or zeolites are known to the skilled person. The skilled person is also aware of the amounts in which stabilizers, molecular sieves, or zeolites can be used.

The process of the invention is optionally carried out in the presence of one or more stabilizers.

Where the process of the invention is carried out in the presence of one or more stabilizers, preference is then given to using one to three stabilizers, more preferably one or two stabilizers, very preferably one (1) stabilizer.

Examples of suitable stabilizers are N-oxides (nitroxyl or N-oxyl radicals), such as 4-hydroxy-2,2,6,6-tetramethylpiperidine-N-oxyl, 4-oxo-2,2,6,6-tetramethylpiperidine-N-oxyl, 4-acetoxy-2,2,6,6-tetramethylpiperidine-N-oxyl, 2,2,6,6-tetramethylpiperidine-N-oxyl, bis(1-oxyl-2,2,6,6-tetramethylpiperidin-4-yl) sebacate, 4,4',4''-tris(2,2,6,6-tetramethylpiperidine-N-oxyl) phosphite, or 3-oxo-2,2,5,5-tetramethylpyrrolidine-N-oxyl; monohydric or polyhydric phenols, optionally having one or more alkyl groups, such as alkylphenols, as for example o-, m- or p-cresol (methylphenol), 2-tert-butylphenol, 4-tert-butylphenol, 2,4-di-tert-butylphenol, 2-methyl-4-tert-butylphenol, 2-tert-butyl-4-methylphenol, 2,6-tert-butyl-4-methylphenol, 4-tert-butyl-2,6-dimethylphenol, or 6-tert-butyl-2,4-dimethylphenol; quinones, such as hydroquinone, hydroquinone monomethyl ether, 2-methylhydroquinone, or 2,5-di-tert-butylhydroquinone; hydroxyphenols, such as, for example, pyrocatechol (1,2-dihydroxybenzene) or benzoquinone; aminophenols, such as p-aminophenol; nitrosophenols, such as p-nitrosophenol; alkoxyphenols, such as, for example, 2-methoxyphenol (guaiacol, pyrocatechol monomethyl ether), 2-ethoxyphenol, 2-isopropoxyphenol, 4-methoxyphenol (hydroquinone monomethyl ether), mono- or di-tert-butyl-4-methoxyphenol; tocopherols, such as α-tocopherol, and also 2,3-dihydro-2,2-dimethyl-7-hydroxybenzofuran (2,2-dimethyl-7-hydroxycumaran), aromatic amines, such as N,N-diphenylamine or N-nitrosodiphenylamine; phenylenediamine, such as N,N'-dialkyl-p-phenylenediamine, where the alkyl radicals may be identical or different and consist in each case independently of one another of 1 to 4 carbon atoms and may be straight-chain or branched, such as N,N'-dimethyl-p-phenylenediamine or N,N'-diethyl-p-phenylene-diamine, hydroxylamines, such as N,N-diethylhydroxylamine, imines, such as methylethylimine or methylene violet, sulfonamides, such as N-methyl-4-toluenesulfonamide or N-tert-butyl-4-toluenesulfonamide, oximes, such as aldoximes, ketoximes, or amide oximes, such as diethyl ketoxime, methyl ethyl ketoxime, or salicylaldoxime, phosphorus-containing compounds, such as triphenylphosphine, triphenyl phosphite, triethyl phosphite, hypophosphorous acid, or alkyl esters of phosphorous acids; sulfur-containing compounds such as diphenyl sulfide or phenothiazine; metal salts, such as salts of copper or of manganese, of cerium, of nickel, or of chromium, examples being their chlorides, sulfates, salicylates, tosylates, acrylates, or acetates, such as copper acetate, copper(II) chloride, copper salicylate, cerium(III) acetate, or cerium(III) ethylhexanoate, for example.

Preferred stabilizers are selected from the group consisting of hydroquinone, hydroquinone monomethyl ether, phenothiazines, 4-hydroxy-2,2,6,6-tetramethylpiperidine-N-oxyl, 4-oxo-2,2,6,6-tetramethylpiperidine-N-oxyl, bis(1-oxyl-2,2,6,6-tetramethylpiperidin-4-yl) sebacate, 2-tert-butylphenol, 4-tert-butylphenol, 2,4-di-tert-butylphenol, 2-tert-butyl-4-methylphenol, 6-tert-butyl-2,4-dimethylphenol, 2,6-di-tert-butyl-4-methylphenol, 2-methyl-4-tert-butylphenol, hypophosphorous acid, copper acetate, copper(II) chloride, copper salicylate, and cerium(III) acetate.

Particularly preferred stabilizers are selected from the group consisting of hydroquinone monomethyl ether, phenothiazine, 2-tert-butyl-4-methylphenol, 6-tert-butyl-2,4-dimethylphenol, 4-hydroxy-2,2,6,6-tetramethylpiperidine-N-oxyl, and 4-oxo-2,2,6,6-tetramethylpiperidine-N-oxyl.

Especially preferred stabilizers are selected from the group consisting of hydroquinone monomethyl ether and phenothiazine.

An especially preferred stabilizer is hydroquinone monomethyl ether.

Where the process of the invention is carried out in the presence of one or more, preferably one to three, more preferably one or two stabilizers, very preferably one (1) stabilizer, each stabilizer is used in general in an amount in the range from 1 to 10 000 ppm, preferably 10 to 5000 ppm, more preferably 30 to 2500 ppm, very preferably 50 to 1500 ppm, based on the amount of compound of the formula (II) employed.

In one particular embodiment of the invention, the process of the invention is carried out in the presence of hydroquinone monomethyl ether as stabilizer, and the hydroquinone monomethyl ether stabilizer is used in general in an amount in the range from 1 to 10 000 ppm, preferably 10 to 5000 ppm, more preferably 30 to 2500 ppm, very preferably 50 to 1500 ppm, based on the amount of compound of the formula (II) employed.

An advantage of using one or more stabilizers, and especially of the use of hydroquinone monomethyl ether as stabilizer, is that it prevents the polymerization of compound of the formula (II) employed and compound of the formula (I) prepared.

The process of the invention is carried out optionally in the presence of one or more molecular sieves.

Where the process of the invention is carried out in the presence of one or more molecular sieves, preference is given to using one to three molecular sieves, more preferably one or two molecular sieves, very preferably one (1) molecular sieve.

Examples of suitable molecular sieves are molecular sieves having a pore size in the range from 3 to 10 angstroms, preferably 3 to 7 angstroms, more preferably 4 to 6 angstroms, very preferably 5 angstroms.

Where the process of the invention is carried out in the presence of one or more, preferably one to three, more preferably one or two molecular sieves, very preferably one (1) molecular sieve, each molecular sieve and the compound of the formula (III) are used in general in a weight ratio of 1:10 to 10:1, preferably of 1:1 to 5:1, more preferably of 1.5:1 to 4:1, very preferably of 2:1 to 3:1.

In one particular embodiment of the invention, the process of the invention is carried out in the presence of a molecular sieve having a pore size of 5 angstroms, and the molecular sieve having a pore size of 5 angstroms and the compound of formula (III) are used in general in a weight ratio of 1:10 to 10:1, preferably of 1:1 to 5:1, more preferably of 1.5:1 to 4:1, very preferably of 2:1 to 3:1.

An advantage of using one or more molecular sieves, more particularly of using a molecular sieve having a pore size of 5 angstroms, is that a higher conversion of compound of the formula (III) employed to compound of the formula (I) prepared is achieved. Any molecular sieve used, more particularly any molecular sieve used having a pore size of 5 angstroms, is able to take up liberated alcohol, such as liberated methanol, and so remove it from the equilibrium.

In one very particular embodiment of the invention, the process of the invention is carried out in the presence of hydroquinone monomethyl ether as stabilizer and in the presence of a molecular sieve having a pore size of 5 angstroms.

In a further very particular embodiment of the invention, the process of the invention is carried out in the presence of hydroquinone monomethyl ether as stabilizer and in the presence of a molecular sieve having a pore size of 5 angstroms, the hydroquinone monomethyl ether stabilizer being used in general in an amount in the range from 1 to 10 000 ppm, preferably 10 to 5000 ppm, more preferably 30 to 2500 ppm, very preferably 50 to 1500 ppm, based on the amount of compound of the formula (II) used, and the molecular sieve having a pore size of 5 angstroms and the compound of formula (III) being used in general in a weight ratio of 1:10 to 10:1, preferably of 1:1 to 5:1, more preferably of 1.5:1 to 4:1, very preferably of 2:1 to 3:1.

In general the process of the invention is carried out at temperatures in the range from 0 to 100° C., preferably 10 to 80° C., more preferably 20 to 60° C., very preferably 30 to 50° C.

Preferably at least one compound of the formula (II) and one compound of the formula (III) are reacted with one another in the presence of at least one enzyme and optionally in the presence of one or more further additives over a period of 1 to 96 hours, more preferably 12 to 72 hours, very preferably 24 to 60 hours.

In one particularly preferred embodiment of the invention, the at least one compound of the formula (II) used functions as solvent.

In an especially preferred embodiment of the invention, methyl acrylate functions as solvent.

In another very particularly preferred embodiment of the invention, methyl methacrylate functions as solvent.

In a further embodiment of the invention, the process of the invention is carried out in the presence of a diluent.

Examples of suitable diluents are $C_3$-$C_6$ alcohols, preferably $C_4$-$C_6$ alcohols, such as tertiary monools, more preferably tert-butanol, tert-amyl alcohol, pyridine, poly-$C_1$-$C_4$ alkylene glycol di-$C_1$-$C_4$ alkyl ethers, preferably polyethylene glycol di-$C_1$-$C_4$ alkyl ethers, such as 1,2-dimethoxyethane, diethylene glycol dimethyl ether, polyethylene glycol dimethyl ether 500, methyl tert-butyl ether, ethyl tert-butyl ether, $C_1$-$C_4$ alkylene carbonates, more particularly propylene carbonate, $C_3$-$C_6$ alkyl acetic acid esters, more particularly tert-butyl acetic acid ester, tetrahydrofuran, toluene, 1,3-dioxolane, acetone, isobutyl methyl ketone, ethyl methyl ketone, 1,4-dioxane, tert-butyl methyl ether, cyclohexane, methylcyclohexane, toluene, hexane, dimethoxymethane, 1,1-dimethoxyethane, or acetonitrile.

Mixtures of these diluents may also be used.

It may be advantageous to remove liberated alcohol by means of a binary or ternary heteroazeotrope which boils very close to the temperature optimum of the enzyme used. The alcohol separated off in this way can then be removed by phase separation or membrane vapor separation.

As a matter of choice it is possible to add aqueous diluents to the organic diluents, resulting—according to the organic diluent—in single-phase or multiphase reaction mixtures. Examples of aqueous diluents are water or aqueous, dilute (e.g., 10 to 100 mM) buffers, having a pH for example in the range from about 6 to 8, such as potassium phosphate buffer or TRIS-HCl buffer, for example.

The reaction mixtures are in general largely anhydrous, meaning that the reaction mixtures comprise in general less than 10, preferably less than 5, more preferably less than 1, and very preferably less than 0.5 vol % of water.

The reactants are preferably used without pretreatment (e.g., drying or water doping).

A diluent is understood in the context of the invention to be an agent which dilutes the at least one compound of the formula (II) used and the compound of the formula (III) used.

In one preferred embodiment of the invention, the process of the invention is carried out in the absence of a diluent.

The process of the invention is preferably carried out in the presence of an oxygen-containing gas, as for example in the presence of air or of an air/oxygen mixture. More preferably the process of the invention is carried out in the presence of air.

The process of the invention is carried out generally at pressures in the range from 0 to 1023 mbar, preferably 500 to 1018 mbar, more preferably 800 to 1013 mbar, very preferably under a pressure of 1013 mbar.

In one especially preferred embodiment of the invention, the process of the invention is carried out at atmospheric pressure. Atmospheric pressure is understood in the context of the invention to be a pressure in the range from 1003 to 1023 mbar, preferably a pressure in the range from 1008 to 1018 mbar, more preferably a pressure of 1013 mbar.

In another embodiment of the invention, the process of the invention is carried out at pressures in the range from 0 to 1013 mbar, preferably 0 to 500 mbar, more preferably 0 to 100 mbar, very preferably 0 to 10 mbar.

In a further embodiment of the invention, the process of the invention is carried out under reduced pressure. Reduced pressure is understood in the context of the invention to be a pressure in the range from 0 to 10 mbar, preferably a pressure in the range from 0 to 5 mbar, more preferably a pressure in the range from 0 to 1 mbar.

The reaction may take place continuously, in a tubular reactor or in a stirred reactor cascade, for example, or discontinuously.

The reaction may take place in all reactors suitable for such a reaction. Reactors of this kind are known to the skilled person. The reaction takes place preferably in a stirred tank reactor or in a fixed bed reactor.

Any desired techniques may be used for mixing. For example, the reaction mixture can be stirred. Special stirring apparatus is unnecessary. The reaction mixture can be shaken, for example. Special shaking apparatus is unnecessary.

If a diluent or mixtures of diluents is or are used, the reactants employed and the additives optionally employed may be optionally introduced in said diluent or said mixtures, being dissolved, suspended, or emulsified therein, for example, and may be admixed with enzyme at the start of the reaction, and also, optionally, one or more times during the reaction course. If no diluent is used, the reactants employed and the additives optionally employed may for example be included in the initial charge and admixed with enzyme at the start of the reaction and also, optionally, one or more times during the reaction course. The temperature at the start of the reaction may be set at the desired level and, if desired, raised or lowered during the reaction course.

If the reaction is carried out in a fixed bed reactor, then the fixed bed reactor is preferably charged with immobilized enzyme, with the reaction mixture being pumped through a column packed with the enzyme. Also possible is the implementation of the reaction in a fluidized bed, in which case the enzyme is used in a form in which it is immobilized on a support. The reaction mixture can be pumped continuously through the column, the dwell time and hence the desired conversion being controllable by the flow rate. It is also possible to pump the reaction mixture in circulation through a column, allowing liberated alcohol to be distilled off at the same time, under reduced pressure, for example.

Liberated alcohol can be removed continuously or in stages in a manner known per se, such as by distillation, reduced pressure, azeotropic removal, absorption, pervaporation, or diffusion via membranes, for example.

The reaction mixtures are worked up by methods known to the skilled person, as for example by filtration (e.g., for the removal of any molecular sieve used) and/or distillation (e.g., for the removal of any compound of the formula (II) used in excess, such as methyl acrylate, ethyl acrylate, methyl methacrylate or ethyl methacrylate). The products are obtained in some cases in the form of viscous oils, which are purified or freed from volatile fractions under reduced pressure and at moderately elevated temperature. Where the products are obtained as solids, purification may also be accomplished by recrystallizing or digesting.

After the end of the reaction, the reaction mixture obtained can be used further without additional purification or can optionally be purified in a further step. In a further purification step, in general, only the enzyme used, diluent optionally used, and any excess of, for example, methyl acrylate, ethyl acrylate, methyl methacrylate or ethyl methacrylate are separated from the reaction mixture obtained. Separating off the enzyme used is accomplished in general by filtration, absorption, centrifugation, or decanting. The enzyme separated off may then be used for further reactions. Separating off any diluent used is accomplished in general by distillation, rectification or, in the case of solid reaction products, by filtration. Chromatography may also be carried out for further purification of the reaction products.

A further subject of the invention is a compound of the formula (Ia),

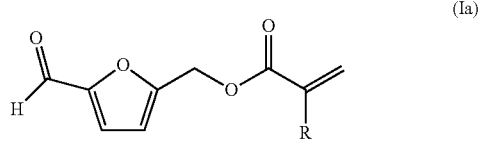

in which R is $C_1$-$C_6$ alkyl.

In one preferred embodiment of the invention, R in the formula (Ia) is $C_1$-$C_4$ alkyl.

In a particularly preferred embodiment of the invention, R in the formula (Ia) is $CH_3$ or $CH_2CH_3$.

In an especially preferred embodiment of the invention, R in the formula (Ia) is $CH_3$.

The compounds of the formula (I), preferably the inventively prepared compounds of the formula (I), or the compounds of the formula (Ia) of the invention are suitable, for example, as comonomers in dispersions and curable compositions.

The HMF structure improves the adhesion properties of, for example coatings to plastics, but also to other materials such as wood or cementitious systems.

The compounds of the formula (I), preferably the compounds of the formula (I) prepared in accordance with the invention, or the compounds of the formula (Ia) of the invention find application, for example, as monomers or comonomers in the production of dispersions which are put to uses including adhesives, coating materials or textile, leather, and paper auxiliaries.

Furthermore, the compounds of the formula (I), preferably the compounds of the formula (I) prepared in accordance with the invention, or the compounds of the formula (Ia) of the invention may find application as comonomers in polymers which are used in turn as additives for fuel oils and lubricants, and in particular as cold flow improvers in fuel oils. Use of this kind is disclosed for example in European patent application EP 1 923 454 A1.

The compounds of the formula (I), preferably the compounds of the formula (I) prepared in accordance with the invention, or the compounds of the formula (Ia) of the invention also find application, for example, as monomers or comonomers in the production of dispersions which are used among other things as printing inks, including liquid printing inks.

The compounds of the formula (I), preferably the compounds of the formula (I) prepared in accordance with the invention, or the compounds of the formula (Ia) of the invention also find application, for example, as monomers or comonomers in the production of dispersions which are used in applications including cosmetics, more particularly care products, such as skin care products, hair care products, or nail care products, for example.

The compounds of the formula (I), preferably the compounds of the formula (I) prepared in accordance with the invention, or the compounds of the formula (Ia) of the invention also find application, for example, as monomers or comonomers in the production of dispersions which are used among other things for coatings in the automobile sector, for industrial coatings, for coatings in the construction of buildings, as adhesives, e.g., pressure-sensitive adhesives, for paper coatings, or as printing inks, including liquid printing inks.

A further subject of the invention, accordingly, is the use of the compounds of the formula (I), preferably of the compounds of the formula (I) prepared in accordance with the invention, or of the compounds of the formula (Ia) of the invention, as monomer or comonomer in the production of a dispersion.

The dispersions produced may comprise one or more compounds of the formula (I), preferably one or more compounds of the formula (I) prepared in accordance with the invention, or one or more compounds of the formula (Ia) of the invention and/or oligomers which have been prepared using one or more compounds of the formula (I), preferably one or more compounds of the formula (I) prepared in accordance with the invention, or one or more compounds of the formula (Ia) of the invention, as monomer or comonomer, and/or polymers which have been prepared using one or more compounds of the formula (I), preferably one or more compounds of the formula (I) prepared in accordance with the invention, or one or more compounds of the formula (Ia) of the invention, as monomer or comonomer.

In one embodiment of the invention, the dispersions produced comprise one or more compounds of the formula (I), preferably one or more compounds of the formula (I) prepared in accordance with the invention, or one or more compounds of the formula (Ia) of the invention.

In a further embodiment of the invention, the dispersions produced comprise oligomers prepared using one or more compounds of the formula (I), preferably one or more compounds of the formula (I) prepared in accordance with the invention, or one or more compounds of the formula (Ia) of the invention, as monomer or comonomer. An oligomer of this kind for the purposes of the invention is composed of 2 to 8 repeating units.

In a further embodiment of the invention, the dispersions produced comprise polymers prepared using one or more compounds of the formula (I), preferably one or more compounds of the formula (I) prepared in accordance with the invention, or one or more compounds of the formula (Ia) of the invention, as monomer or comonomer. A polymer of this kind for the purposes of the invention is composed of $\geq 9$, preferably $\geq 50$, more preferably $\geq 100$, very preferably $\geq 1000$ repeating units.

In one preferred embodiment of the invention, the dispersions produced have a low monomer content, which in the context of the invention means that the dispersions produced comprise 0 to 5 wt %, preferably 0 to 2 wt %, more preferably 0 to 1 wt %, very preferably 0 to 0.1 wt % of compounds of the formula (I), preferably compounds of the formula (I) prepared in accordance with the invention, or compounds of the formula (Ia) of the invention (based on the sum of the compounds of the formulae (I) or (Ia) comprised in the dispersions produced; oligomers prepared using compounds of the formulae (I) or (Ia) as monomer or comonomer; and polymers prepared using compounds of the formulae (I) or (Ia) as monomer or comonomer).

In another preferred embodiment of the invention, the dispersions produced have a low oligomer content, which in the context of the invention means that the dispersions produced comprise 0 to 5 wt %, preferably 0 to 2 wt %, more preferably 0 to 1 wt %, very preferably 0 to 0.1 wt % of oligomers prepared using one or more compounds of the formula (I), preferably one or more compounds of the formula (I) prepared in accordance with the invention, or one or more compounds of the formula (Ia) of the invention as monomer or comonomer (based on the sum of the compounds of the formulae (I) or (Ia) comprised in the dispersions produced; oligomers prepared using compounds of the formulae (I) or (Ia) as monomer or comonomer; and polymers prepared using compounds of the formulae (I) or (Ia) as monomer or comonomer).

In a particularly preferred embodiment of the invention, the dispersions produced have a high polymer content, which in the context of the invention means that the dispersions produced comprise 90 to 100 wt %, preferably 96 to 100 wt %, more preferably 98 to 100 wt %, very preferably 99.8 to 100 wt % of polymers prepared using one or more compounds of the formula (I), preferably one or more compounds of the formula (I) prepared in accordance with the invention, or one or more compounds of the formula (Ia) of the invention as monomer or comonomer (based on the sum of the compounds of the formulae (I) or (Ia) comprised in the dispersions produced; oligomers prepared using compounds of the formulae (I) or (Ia) as monomer or comonomer; and polymers prepared using compounds of the formulae (I) or (Ia) as monomer or comonomer).

In one especially preferred embodiment of the invention, the dispersions produced have a low monomer content, a low oligomer content, and a high polymer content. The terms "low monomer content", "low oligomer content", and "high polymer content" have been defined above.

In one embodiment of the invention, the dispersions produced are used as adhesives, coating materials, textile, leather, or paper auxiliaries, or as additive for fuel oils and lubricants.

A further subject of the invention, accordingly, is the use of the dispersions produced, the dispersions being used as adhesives, coating materials, textile, leather or paper auxiliaries or as additive for fuel oils and lubricants.

In one embodiment of the invention the dispersions produced are used as printing inks, including liquid printing inks.

A further subject of the invention, accordingly, is the use of the dispersions produced, the dispersions being used as printing inks, including liquid printing inks.

In one embodiment of the invention, the dispersions produced are used in cosmetics, more particularly as care products, such as skin care products, hair care products, or nail care products, for example.

A further subject of the invention, accordingly, is the use of the dispersions produced, the dispersions being used in cosmetics, more particularly as care products, such as skin care products, hair care products, or nail care products, for example.

In one embodiment of the invention, the dispersions produced are used for coatings in the automobile sector, for industrial coatings, for coatings in the construction of buildings, as adhesives, e.g., pressure-sensitive adhesives, for paper coatings, or as printing inks, including liquid printing inks.

A further subject of the invention accordingly is the use of the dispersions produced, the dispersions being used for coatings in the automobile sector, for industrial coatings, for coatings in the construction of buildings, as adhesives, e.g., pressure-sensitive adhesives, for paper coatings, or as printing inks, including liquid printing inks.

In one embodiment of the invention, the dispersions produced are used for coatings, more particularly coatings in the automobile sector, industrial coatings, or coatings in the construction of buildings, as adhesives, as printing inks, including liquid printing inks, or in cosmetics.

A further subject of the invention, accordingly, is the use of the dispersions produced, the dispersions being used for coatings, especially coatings in the automobile sector, industrial coatings, or coatings in the construction of buildings, as adhesives, as printing inks, including liquid printing inks, or in cosmetics.

The dispersions produced may also be used, for example, for interior or exterior coatings, such as coatings on walls, floors, or ceilings, for example, and also more particularly as wall paints, paints for floors, or paints for ceilings.

The dispersions produced can also be used, for example, for coatings on masonry, both interiorly and exteriorly.

The dispersions produced can also be used for traffic markings, for example.

An advantage of the compounds of the formula (I), preferably of the compounds of the formula (I) prepared in accordance with the invention, or of the compounds of the formula (Ia) of the invention is that on account of their low color number they can be employed in coatings applications, and especially advantageously in clearcoat materials therein, since their low inherent coloration means that they produce reduced coloring of the coatings relative to (meth)acrylates prepared by conventional processes.

Furthermore, coatings with the compounds of the formula (I), preferably the compounds of the formula (I) prepared in accordance with the invention, or the compounds of the formula (Ia) of the invention may have very high scratch resistances, hardnesses, chemical resistances, elasticity, and adhesion, on both hydrophilic and hydrophobic substrates.

The compounds of the formula (I), preferably the compounds of the formula (I) prepared in accordance with the invention, or the compounds of the formula (Ia) of the invention can be used advantageously as monomers or comonomers in poly(meth)acrylates or as reactive diluents in thermally curable, radiation-curable and/or dual-cure-curable poly(meth)acrylates. Poly(meth)acrylates of these kinds are suitable for example as binders in thermally curable, radiation-curable or dual-cure-curable coating materials, and also in adhesives, such as in acrylate adhesives, for example, and also in sealants.

A further subject of the invention, therefore, is the use of the compounds of the formula (I), preferably of the compounds of the formula (I) prepared in accordance with the invention, or of the compounds of the formula (Ia) of the invention as reactive diluents or binders in radiation-curable or dual-cure-curable coating compositions, preferably in topcoats, more preferably in transparent clear coat materials. The compounds of the formula (I), preferably the compounds of the formula (I) prepared in accordance with the invention, or the compounds of the formula (Ia) of the invention can of course also be used as monomers in polymerizations, optionally together with other polymerizable monomers, such as, for example, (meth)acrylic acid, (meth)acrylic esters, styrene, butadiene, acrylonitrile, vinyl acetate, N-vinylpyrrolidone, 4-hydroxybutyl vinyl ether, or N-vinylformamide.

"Dual cure" means that the coating compositions are curable thermally and with actinic radiation. Actinic radiation for the purposes of the present invention means electromagnetic radiation such as visible light, UV radiation, or X-rays, especially UV radiation, and particulate radiation such as electron beams.

Radiation-curable binders are those which can be cured by means of actinic radiation as defined above, more particularly by means of UV radiation.

A further subject of the invention are coating formulations comprising the compounds of the formula (I), preferably the compounds of the formula (I) prepared in accordance with the invention, or the compounds of the formula (Ia) of the invention. These compounds of the formula (I), preferably the compounds of the formula (I) prepared in accordance with the invention, or the compounds of the formula (Ia) of the invention can be used not only in basecoat materials but also in topcoat materials. On account of their particular properties, especially their low color number, their use in topcoat systems and in radiation-cured clearcoat systems is preferred.

Besides the compounds of the formula (I), preferably the compounds of the formula (I) prepared in accordance with the invention, or the compounds of the formula (Ia) of the invention, a radiation-curable composition of the invention may also comprise the following components:

(G) at least one polymerizable compound having two or more copolymerizable ethylenically unsaturated groups,
(H) optionally reactive diluents,
(P) optionally photoinitiators, and
(J) optionally further, typical coatings additives.

Compounds (G) contemplated include radiation-curable, radically polymerizable compounds having two or more, i.e., at least two, copolymerizable ethylenically unsaturated groups.

Reactive diluents contemplated (compounds (H)) include radiation-curable, radically or cationically polymerizable compounds having only one ethylenically unsaturated copolymerizable group.

As photoinitiators (P) it is possible to use photoinitiators known to the skilled person, examples being those specified in "Advances in Polymer Science", Volume 14, Springer Berlin 1974 or in K. K. Dietliker, Chemistry and Technology of UV and EB Formulation for Coatings, Inks and Paints, Volume 3; Photoinitiators for Free Radical and Cationic Polymerization, P. K. T. Oldring (ed.), SITA Technology Ltd, London.

As further, typical coatings additives (J) it is possible to make use, for example, of antioxidants, oxidation inhibitors, stabilizers, activators (accelerators), fillers, pigments, dyes, degassing agents, luster agents, antistatic agents, flame retardants, thickeners, thixotropic agents, flow control assistants, binders, antifoam agents, fragrances, surface-active agents, viscosity modifiers, plasticizers, tackifying resins (tackifiers), chelating agents, or compatibilizers.

Examples of the stated classes of compound (G), (H), (P), and (J) are disclosed in WO 2006/005491 and in DE 10 2005 037 430. Both specifications are hereby expressly referenced.

Typical constitutions for radiation-curable compositions are for example
(I) or (Ia) 20-100 wt %, preferably 40-90, more preferably 50-90, more particularly 60-80 wt %,
(G) 0-60 wt %, preferably 5-50, more preferably 10-40, more particularly 10-30 wt %,
(H) 0-50 wt %, preferably 5-40, more preferably 6-30, more particularly 10-30 wt %,
(P) 0-20 wt %, preferably 0.5-15, more preferably 1-10, more particularly 2-5 wt %, and
(J) 0-50 wt %, preferably 2-40, more preferably 3-30, more particularly 5-20 wt %,
with the proviso that (I) or (Ia), (G), (H), (P), and (J) together make 100 wt %.

The substrates are coated by customary methods known to the skilled person, in which at least one coating composition is applied in the desired thickness to the substrate that is to be coated, and the volatile constituents, where present, in the coating composition are removed, optionally with heating. This operation can if desired be repeated one or more times. Application to the substrate may take place in a known way, as for example by spraying, trowelling, knifecoating, brushing, rolling, roller coating, pouring, laminating, injection backmolding, or coextruding. The thickness of coating is generally in a range from about 3 to 1000 g/m$^2$ and preferably 10 to 200 g/m$^2$.

The compounds of the formula (I), preferably the compounds of the formula (I) prepared in accordance with the invention, or the compounds of the formula (Ia) of the invention can also be used advantageously, on account of their relatively low coloration, in a thermally induced (radical) (co)polymerization.

Monomers with which the compounds of the formula (I), preferably the compounds of the formula (I) prepared in accordance with the invention, or the compounds of the formula (Ia) of the invention can be copolymerized, for example, include, for example, $C_1$-$C_{20}$ alkyl (meth)acrylates, vinylaromatics having upto 20 C atoms, vinyl esters of carboxylic acids comprising up to 20 C atoms, ethylenically unsaturated nitriles, vinyl ethers of alcohols comprising 1 to 10 C atoms, and aliphatic hydrocarbons having 2 to 8 C atoms and 1 or 2 double bonds.

Preferred (meth)acrylic acid alkyl esters are those having a $C_1$-$C_{10}$ alkyl radical, such as methyl methacrylate, methyl acrylate, n-butyl acrylate, ethyl acrylate, and branched alkyl derivatives such as 2-ethylhexyl acrylate.

In particular, mixtures of the (meth)acrylic acid alkyl esters are also suitable.

Vinyl esters of carboxylic acids with 1 to 20 C atoms are, for example, vinyl laurate, vinyl stearate, vinyl propionate, and vinyl acetate.

Vinylaromatic compounds contemplated include, for example, vinyltoluene, α-butylstyrene, 4-n-butylstyrene, 4-n-decylstyrene, and—preferably—styrene.

Examples of nitriles are acrylonitrile and methacrylonitrile.

Suitable vinyl ethers are, for example, vinyl methyl ether, vinyl isobutyl ether, vinyl hexyl ether, and vinyl octyl ether.

Nonaromatic hydrocarbons having 2 to 8 C atoms and one or two olefinic double bonds include butadiene, isoprene, and also ethylene, propylene, and isobutylene.

Monomers with which the compounds of the formula (I), preferably the compounds of the formula (I) prepared in accordance with the invention, or the compounds of the formula (Ia) of the invention can be copolymerized, for example, include vinyl monomers such as, for example, 1,3-butadiene, isoprene, styrene, substituted styrenes, divinylbenzene, heterocyclic vinyl compounds or vinyl halides; vinyl esters such as vinyl formate, vinyl acetate, vinyl propionate, vinyl versatate, or vinyl laurate; vinyl ethers such as methyl vinyl ether, ethyl vinyl ether, vinyl 2-methoxy ethyl ether, or vinyl 2-chloroethyl ether; (meth) acrylic esters with $C_1$-$C_{24}$ alcohols, such as methyl (meth) acrylate, ethyl (meth)acrylate, butyl (meth)acrylate, 2-ethylhexyl (meth)acrylate, isopropyl (meth)acrylate, hydroxyethyl (meth)acrylate, hydroxypropyl (meth)acrylate, n- or isopropyl (meth)acrylate, amyl (meth)acrylate, isoamyl (meth)acrylate, tert-amyl (meth)acrylate, hexyl (meth)acrylate, cyclohexyl (meth)acrylate, octyl (meth) acrylate, decyl (meth)acrylate, lauryl (meth)acrylate, myristyl (meth)acrylate, cetyl (meth)acrylate, stearyl (meth)acrylate; (meth)acrylic esters of ether alcohols, such as ethylene glycol monomethyl ether(meth)acrylate, for example, and also di(meth)acrylates of $C_1$-$C_6$ diols, such as 1,6-hexanediol di(meth)acrylate, or (meth)acrylic acid and/or other vinylically unsaturated carboxylic acids, carboxamides, or carbonitriles.

A frequent method, though not the only one, for preparing such (co)polymers is that of radical or ionic (co)polymerization in a solvent or diluent.

The radical (co)polymerization of such monomers takes place for example in aqueous solution in the presence of polymerization initiators which under polymerization conditions break down into radicals, examples being peroxodisulfates, $H_2O_2$ redox systems, or hydroperoxides, such as tert-butyl hydroperoxide or cumene hydroperoxide, for example. The (co)polymerization may be carried out within a wide temperature range, optionally under reduced pressure or else under elevated pressure, in general at temperatures of up to 100° C. The pH of the reaction mixture is commonly adjusted to a level in the range from 4 to 10.

The (co)polymerization can alternatively be carried out continuously or discontinuously in another manner known per se to the skilled person, in the form, for example, of a solution, precipitation, water-in-oil emulsion, inverse emulsion, suspension or inverted suspension polymerization.

The monomer or monomers here are (co)polymerized using radical polymerization initiators, examples being azo compounds which break down into radicals, such as 2,2'-azobis(isobutyronitrile), 2,2'-azobis(2-amidinopropane) hydrochloride, or 4,4'-azobis(4'-cyanopentanoic acid), or dialkyl peroxides, such as di-tert-amyl peroxide, aryl alkyl peroxides, such as tert-butyl cumyl peroxide, alkyl acyl peroxides, such as tert-butyl peroxy-2-ethylhexanoate, peroxydicarbonates, such as di(4-tert-butylcyclohexyl)peroxydicarbonate, or hydroperoxides.

Further examples of suitable polymerization initiators are peroxides, hydroperoxides, hydrogen peroxide, persulfates, azo compounds, or the so-called redox initiators.

Further examples of suitable polymerization initiators are acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, di(2-ethylhexyl) peroxydicarbonate, dicyclohexyl peroxydicarbonate, di(4-tert-butylcyclohexyl) peroxydicarbonate, dimyristyl peroxydicarbonate, diacetyl peroxydicarbonate, allyl peresters, cumyl peroxyneodecanoate, tert-butyl per-3,5,5-trimethylhexanoate, acetyl cyclohexylsulfonyl peroxide, dilauryl peroxide, dibenzoyl peroxide, or tert-amyl perneodecanoate.

Examples of preferred polymerization initiators are azo compounds, examples being 2,2'-azobisisobutyronitrile, 2,2'-azobis(2,4-dimethylvaleronitrile), and 2,2'-azobis(4-methoxy-2,4-dimethylvaleronitrile).

The stated compounds are used usually in the form of aqueous solutions or aqueous emulsions, with the lower concentration being determined by the amount of water that is acceptable in the (co)polymerization, and the upper concentration being determined by the solubility of the respective compound in water.

Serving as solvents or diluents may be, for example, water, alcohols, such as methanol, ethanol, n- or isopropanol, n- or isobutanol, or ketones, such as acetone, ethyl methyl ketone, diethyl ketone, or isobutyl methyl ketones. Particularly preferred are apolar solvents, such as, for example, xylene and its isomer mixtures, Shellsol® A and solvent naphtha.

In one preferred embodiment, the monomers are added in premixed form and initiator with any further additions is added in solution in solvent. A particularly preferred embodiment is described in WO 2001/23484, particularly at page 10, line 3 to line 24 therein.

The (co)polymerization may optionally be carried out in the presence of chain transfer agents, such as, for example, hydroxylammonium salts, chlorinated hydrocarbons, and thio compounds, such as tert-butyl mercaptan, thioglycolic acid ethylacryl ester, mercaptoethanol, mercaptopropyltrimethoxysilane, dodecyl mercaptan, tert-dodecyl mercaptan, or alkali metal hypophosphites, for example. In the (co)polymerization, these chain transfer agents may be used, for example, in amounts of 0 to 0.8 part by weight, based on 100 parts by weight of the monomers to be (co)polymerized, and they lower the molar mass of the resulting (co)polymer.

In the emulsion polymerization it is possible to use dispersants, ionic and/or nonionic emulsifiers and/or protective colloids or stabilizers as surface-active compounds. Contemplated as such are not only the protective colloids commonly used for the implementation of emulsion polymerizations, but also emulsifiers.

Examples of suitable protective colloids are polyvinyl alcohols, cellulose derivatives, or vinylpyrrolidone-comprising copolymers. A comprehensive description of further suitable protective colloids is found in Houben-Weyl, Methoden der organischen Chemie, Volume XIV/1, Makromolekulare Stoffe, Georg-Thieme-Verlag, Stuttgart, 1969, pp. 411 to 420. It will be appreciated that mixtures of emulsifiers and/or protective colloids may also be used. As dispersants it is preferred to use exclusively emulsifiers, whose relative molecular weights, unlike those of the protective colloids, are usually below 1000. They may be anionic, cationic or nonionic in nature. Where mixtures of surface-active substances are used, the individual components must of course be compatible with one another, something which in case of doubt can be checked by means of a few preliminary tests. Generally speaking, anionic emulsifiers are compatible with one another and with nonionic emulsifiers.

The same applies to cationic emulsifiers, whereas anionic and cationic emulsifiers are usually incompatible with one another. Examples of customary emulsifiers are ethoxylated mono-, di-, and tri-alkylphenols (EO degree: 3 to 100, alkyl radical: $C_4$ to $C_{12}$), ethoxylated fatty alcohols (EO degree: 3 to 100, alkyl radical: $C_8$ to $C_{18}$), and also alkali metal salts and ammonium salts of alkyl sulfates (alkyl radical: $C_8$ to $C_{16}$), of sulfuric monoesters with ethoxylated alkylphenols (EO degree: 3 to 100, alkyl radical: $C_4$ to $C_{12}$), of alkylsulfonic acids (alkyl radical: $C_{12}$ to $C_{18}$), and of alkylacrylsulfonic acids (alkyl radical: $C_9$ to $C_{18}$). Further suitable emulsifiers such as sulfosuccinic esters are found in Houben-Weyl, Methoden der organischen Chemie, Volume XIV/1, Makromolekulare Stoffe, Georg-Thieme Verlag, Stuttgart, 1961, pages 192 to 208.

In general the amount of dispersant used is 0.5 to 6 wt %, preferably 1 to 3 wt %, based on the monomers for radical polymerization.

Examples of (meth)acrylate-containing dispersions are n-butyl acrylate/acrylonitrile dispersions which find application as adhesives, and also n-butyl acrylate/butadiene/styrene dispersions.

The polymer dispersions in which the compounds of the formula (I), preferably the compounds of the formula (I) prepared in accordance with the invention, or the compounds of the formula (Ia) of the invention are used, may additionally be chemically and/or physically deodorized.

Chemical deodorization may be carried out for example as disclosed by P. H. H. Araújo, C. Sayer, J. G. R. Poco, R. Giudici in Polymer Engineering and Science, 2002 (42), 1442-1468, or in EP 1 375 530 B1.

The copolymers obtainable with the compounds of the formula (I), preferably with the compounds of the formula (I) prepared in accordance with the invention, or with the compounds of the formula (Ia) of the invention generally have a relatively low color number, this being advantageous in the coatings field. The copolymers described can then be reacted in a conventional way, for example with amino resins, such as melamine, for example, to give crosslinked coating resins, as is described in EP 0 738 740 or EP 0 675 141, for example.

The coating compositions are suitable with particular preference as or in exterior coatings, in other words those applications involving daylight exposure, preferably on buildings or parts of buildings, interior coatings, traffic markings, coatings on vehicles and aircraft. The coatings in particular may also be used as wood, paper, or plastics coatings, for wood flooring or furniture, for example.

A further subject of the invention is the use of the compounds of the formula (I), preferably of the compounds of the formula (I) prepared in accordance with the invention, or of the compounds of the formula (Ia) of the invention, as precursor for bright electroplating additives. Their reduced color number by comparison with conventionally obtainable products makes them extremely suitable for this application.

A further subject of the invention is the use of the compounds of the formula (I), preferably of the compounds of the formula (I) prepared in accordance with the invention, or of the compounds of the formula (Ia) of the invention, as monomer or comonomer in poly(meth)acrylates or as reactive diluents in thermally curable, radiation-curable and/or dual-cure-curable poly(meth)acrylates, more particularly in dual-cure-curable coating compositions, or as a precursor for bright electroplating additives.

A further subject of the invention is the use of the compounds of the formula (I), preferably of the compounds of the formula (I) prepared in accordance with the invention, or of the compounds of the formula (Ia) of the invention, as reactive diluents in thermally curable, radiation-curable and/or dual-cure-curable poly(meth)acrylates, more particularly in dual-cure-curable coating compositions.

The compounds of the formula (I), preferably the compounds of the formula (I) prepared in accordance with the invention, or the compounds of the formula (Ia) of the invention are also suitable as comonomers in postcrosslinkable systems.

Postcrosslinkable systems are described in, for example, Iranian Polymer Journal 2008, 17 (7), 555-564 and Progress in Polymer Science 2011, 36, 191-217.

A further subject of the invention is the use of the compounds of the formula (I), preferably of the compounds of the formula (I) prepared in accordance with the invention, or of the compounds of the formula (Ia) of the invention, for the preparation of a crosslinkable copolymer.

For example, the compounds of the formula (I), preferably the compounds of the formula (I) prepared in accordance with the invention, or the compounds of the formula (Ia) of the invention, are suitable for use in combination with crosslinking-active comonomers in self-crosslinking resins. Suitable crosslinking-active comonomers for use in self-crosslinking resins are comonomers whose functional side groups are able to react with the aldehyde-functional monomers of the invention, examples being amines, hydrazines, or oxime-blocked isocyanates. Comonomers of these kind are described in EP 2246403 or in DE 4237030, for example.

The compounds of the formula (I), preferably the compounds of the formula (I) prepared in accordance with the invention, or the compounds of the formula (Ia) of the invention are also suitable for use in resins wherein the crosslinking function is not incorporated in the polymer component itself, but instead a separate crosslinker is added. Typically use is made here, for example, of amines, diamines, triamines, hydroxylamines, oximes, oxime ethers, oxyamines, dihydrazines, dihydrazides, trihydrazides, or polyhydrazides. Further suitable crosslinkers are described in WO 2006/086322, for example.

The amount in which the compounds of the formula (I), preferably the compounds of the formula (I) prepared in accordance with the invention, or the compounds of the formula (Ia) of the invention, are used in the copolymers is generally 0.2 to 35 wt %, preferably 0.5 to 20 wt %, more preferably 1 to 10 wt %. The amount in which the crosslinking-active comonomers are used in each case may be harmonized with the previous amount on a molar basis. The same applies with regard to the amount of the separate crosslinkers used.

The crosslinkable systems find application, for example, in the production of coatings, adhesives, and films for porous and nonporous substrates such as paper, non-woven materials, textiles, leather, wood, concrete, masonry, metals with or without priming, plastics (e.g., polypropylene, polyesters, polyurethanes), building materials, articles made from polymers, protective finishes.

The crosslinkable systems also find application, for example, in the production of fiber materials, films, sheets, composites, inks, print binders, flocking materials, adhesives, care products, such as skin care products, hair care products, or nail care products, for example.

The crosslinkable systems also find application, for example, in the production of scratch-resistant protective coats for interior or exterior use, such as plastics coatings for vehicles, electrical appliances, or wooden floors, for example.

The crosslinkable systems also find application, for example, in the coating or impregnation of carpets or textiles, which may be used for clothing, upholstered furniture, tents, marquees, and the like. Suitable textiles include fabrics, yarns or blended textiles, irrespective of whether they are woven or nonwoven or knitted, and whether they are natural, synthetic or regenerated. Examples of suitable textiles include cellulose acetate, acrylic, wool, cotton, jute, linen, polyesters, polyamides, regenerated cellulose (rayon), and the like.

The invention is elucidated in more detail by the examples which follow.

EXAMPLES

The 5-(hydroxymethyl)furfural (HMF) used in the synthesis examples was acquired commercially from Aldrich (CAS: 67-47-0).

The methyl acrylate and methyl methacrylate used in the synthesis examples were acquired from BASF.

The BASF Novozym® 435 enzyme used in the synthesis examples was acquired from BASF.

The term HMF-acrylate used in the synthesis examples stands for the compound depicted below:

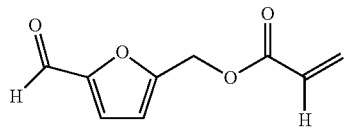

The term HMF-methacrylate used in the synthesis examples stands for the compound depicted below:

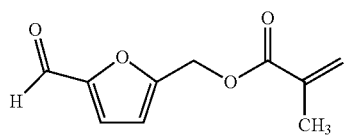

The term MEHQ used in the synthesis examples stands for "monomethyl ether of hydroquinone" or hydroquinone monomethyl ether. A synonym thereof is para-methoxyphenol (PMP).

Gas chromatography:
Gas-chromatic observation of the progress of reaction took place according to the following method:
Instrument: Agilent 6890N
Column: RTX-200-MS$_{length}$=30 m, $\emptyset_{internal}$=0.32 mm, $\emptyset_{external}$=0.45 mm, film thickness 0.5 μm; from Restec, order No.: 15639
Flow rate: 1.0 mL/min at 5.7 PSI (measured at oven temp. of 80° C.)
Split: 1:50, split flow: 50 mL/min, septum purge 3.0 mL/min (measured at oven temp. of 80° C.)
Carrier gas: nitrogen
Injector: split/splitless with siltec-deactivated liner (from Restec #20782-213.5)
Injector temperature: 280° C.
Injection volume: 1 μL
Detector: FID with 300 mL/min air, 30 mL/min hydrogen, and 30 mL/min make-up gas (nitrogen)
Detector temperature: 320° C.
Temperature program:
Start: 60° C.
Dwell time 1: 5 min
Temperature ramp 1: 15° C./min
End temperature 1: 310° C.
Dwell time 2: 10 min
Total run time: 31.7 min
Measurements and results: diluted samples according to area % without solvent and acrylate
Analysis: Empower 3 software Service Release 1 (from Waters)

Example 1

In a 25 mL Schott flask, HMF (1 g, 0.0079 mol) was dissolved in methyl acrylate (6.83 g, 0.079 mol). Added to this batch were molecular sieve (2.5 g, 5 angstroms) and a spatula tip of MEHQ. The batch was admixed with the enzyme BASF Novozym® 435 (0.075 g, 7.5 wt %) and shaken on a water bath at a reaction temperature of 40° C. The reaction progress was observed via gas chromatography:

| Entry | Time [h] | Reactant: HMF (retention time: 14.1 min) | Product: HMF acrylate (retention time: 15.5 min) |
|---|---|---|---|
| 1 | 2 | 91.26 | 8.74 |
| 2 | 4 | 88.28 | 11.72 |
| 3 | 24 | 64.4 | 35.6 |
| 4 | 48 | 23.4 | 76.6 |

After 48 hours, a conversion (of HMF to HMF-acrylate) of 76.6% was shown. The reaction was extremely selective, with no formation of byproducts, and without coloration of the reaction batch. Following filtration to remove the molecular sieve, the batch was amenable to concentration under reduced pressure (removal of the volatile methyl acrylate). The reaction residue obtained was colorless.

The identity of the product was verified via GC-MS (mass$_{theoretical}$: 180.6 (C$_9$H$_8$O$_4$); mass$_{found}$: 180) and also by 1H NMR.

Example 2

In a 25 mL Schott flask, HMF (1 g, 0.0079 mol) was dissolved in methyl methacrylate (7.9 g, 0.079 mol). Added to this batch were molecular sieve (2.5 g, 5 angstroms) and also a spatula tip of MEHQ. The batch was admixed with the enzyme BASF Novozym® 435 (0.075 g, 7.5 wt %) and shaken on a water bath at a reaction temperature of 40° C. The reaction progress was observed via gas chromatography. After 48 hours a conversion (of HMF to HMF-methacrylate) of 6% was shown.

What is claimed is:

1. A process for preparing a compound of the formula (I),

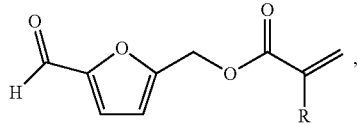

wherein R is H or $C_1$-$C_6$ alkyl,
the process comprising:
reacting at least one compound of the formula (II)

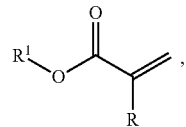

wherein R is H or $C_1$-$C_6$ alkyl, and $R^1$ is H, $C_1$-$C_{12}$ alkyl or $C_3$-$C_{12}$ cycloalkyl, with a compound of the formula (III)

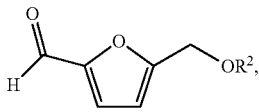

wherein $R^2$ is H or $C(O)R^3$, and $R^3$ is H or $C_1$-$C_{12}$ alkyl, in the presence of at least one enzyme suitable for transesterification, and in the presence of at least one stabilizer.

2. The process according to claim 1, where R is H or $CH_3$.

3. The process according to claim 1, where R is H.

4. The process according to claim 1, where R is $CH_3$.

5. The process according to claim 1, where $R^1$ is $CH_3$ or $CH_2CH_3$.

6. The process according to claim 1, where $R^2$ is H.

7. The process according to claim 1, wherein the at least one enzyme comprises a hydrolase (EC 3.-.-.-).

8. The process according to claim 1, wherein the at least one enzyme comprises a lipase(EC 3.1.1.-).

9. The process according to claim 1, wherein the at least one compound of the formula (II) and the compound of the formula (III) are reacted in a molar ratio of 5:1 to 15:1.

10. The process according to claim 1, wherein the process is carried out at a temperature of from 20 to 60° C.

11. The process according to claim 1, wherein $R^2$ is $C(O)R^3$ and/or R is $C_1$-$C_6$ alkyl.

* * * * *

SEQUENCE LISTING

<160> NUMBER OF SEQ ID NOS: 2

<210> SEQ ID NO 1
<211> LENGTH: 342
<212> TYPE: PRT
<213> ORGANISM: Candida antarctica

<400> SEQUENCE: 1

Met Lys Leu Leu Ser Leu Thr Gly Val Ala Gly Val Leu Ala Thr Cys
1               5                   10                  15

Val Ala Ala Thr Pro Leu Val Lys Arg Leu Pro Ser Gly Ser Asp Pro
            20                  25                  30

Ala Phe Ser Gln Pro Lys Ser Val Leu Asp Ala Gly Leu Thr Cys Gln
        35                  40                  45

Gly Ala Ser Pro Ser Ser Val Ser Lys Pro Ile Leu Leu Val Pro Gly
    50                  55                  60

Thr Gly Thr Thr Gly Pro Gln Ser Phe Asp Ser Asn Trp Ile Pro Leu
65                  70                  75                  80

Ser Thr Gln Leu Gly Tyr Thr Pro Cys Trp Ile Ser Pro Pro Pro Phe
                85                  90                  95

Met Leu Asn Asp Thr Gln Val Asn Thr Glu Tyr Met Val Asn Ala Ile
            100                 105                 110

Thr Ala Leu Tyr Ala Gly Ser Gly Asn Asn Lys Leu Pro Val Leu Thr
        115                 120                 125

Trp Ser Gln Gly Gly Leu Val Ala Gln Trp Gly Leu Thr Phe Phe Pro
    130                 135                 140

Ser Ile Arg Ser Lys Val Asp Arg Leu Met Ala Phe Ala Pro Asp Tyr
145                 150                 155                 160

Lys Gly Thr Val Leu Ala Gly Pro Leu Asp Ala Leu Ala Val Ser Ala
                165                 170                 175

Pro Ser Val Trp Gln Gln Thr Thr Gly Ser Ala Leu Thr Thr Ala Leu
            180                 185                 190

Arg Asn Ala Gly Gly Leu Thr Gln Ile Val Pro Thr Thr Asn Leu Tyr
        195                 200                 205

Ser Ala Thr Asp Glu Ile Val Gln Pro Gln Val Ser Asn Ser Pro Leu
    210                 215                 220

Asp Ser Ser Tyr Leu Phe Asn Gly Lys Asn Val Gln Ala Gln Ala Val
225                 230                 235                 240

Cys Gly Pro Leu Phe Val Ile Asp His Ala Gly Ser Leu Thr Ser Gln
                245                 250                 255

Phe Ser Tyr Val Val Gly Arg Ser Ala Leu Arg Ser Thr Thr Gly Gln
            260                 265                 270

Ala Arg Ser Ala Asp Tyr Gly Ile Thr Asp Cys Asn Pro Leu Pro Ala
        275                 280                 285

Asn Asp Leu Thr Pro Glu Gln Lys Val Ala Ala Ala Leu Leu Ala
    290                 295                 300

Pro Ala Ala Ala Ala Ile Val Ala Gly Pro Lys Gln Asn Cys Glu Pro
305                 310                 315                 320

Asp Leu Met Pro Tyr Ala Arg Pro Phe Ala Val Gly Lys Arg Thr Cys
                325                 330                 335

Ser Gly Ile Val Thr Pro
            340

<210> SEQ ID NO 2
<211> LENGTH: 317

```
<212> TYPE: PRT
<213> ORGANISM: Candida antarctica

<400> SEQUENCE: 2

Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
            20                  25                  30

Pro Ile Leu Leu Val Pro Gly Thr Gly Thr Thr Gly Pro Gln Ser Phe
        35                  40                  45

Asp Ser Asn Trp Ile Pro Leu Ser Thr Gln Leu Gly Tyr Thr Pro Cys
    50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Ala Leu Tyr Ala Gly Ser Gly Asn
                85                  90                  95

Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Thr Val Leu Ala Gly Pro Leu
    130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
            180                 185                 190

Gln Val Ser Asn Ser Pro Leu Asp Ser Ser Tyr Leu Phe Asn Gly Lys
        195                 200                 205

Asn Val Gln Ala Gln Ala Val Cys Gly Pro Leu Phe Val Ile Asp His
    210                 215                 220

Ala Gly Ser Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ala Ala Ala Ile Val Ala Gly
        275                 280                 285

Pro Lys Gln Asn Cys Glu Pro Asp Leu Met Pro Tyr Ala Arg Pro Phe
    290                 295                 300

Ala Val Gly Lys Arg Thr Cys Ser Gly Ile Val Thr Pro
305                 310                 315
```